(12) United States Patent
Gopinathan et al.

(10) Patent No.: US 8,285,560 B2
(45) Date of Patent: *Oct. 9, 2012

(54) METHOD FOR REMOTE MEDICAL CONSULTATION AND CARE

(75) Inventors: Govindan Gopinathan, Oradell, NJ (US); Arthur R. Tilford, Yorba Linda, CA (US); Michael Makover, Great Neck, NY (US)

(73) Assignee: Ineedmd.com, Inc., Great Neck, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/977,654

(22) Filed: Dec. 23, 2010

(65) Prior Publication Data

US 2011/0092825 A1 Apr. 21, 2011

Related U.S. Application Data

(63) Continuation of application No. 10/310,334, filed on Dec. 5, 2002, now Pat. No. 7,860,725, which is a continuation-in-part of application No. 09/884,371, filed on Jun. 19, 2001, now Pat. No. 6,595,918, and a continuation-in-part of application No. 09/741,283, filed on Dec. 19, 2000, now Pat. No. 6,540,673, said application No. 09/884,371 is a continuation of application No. 09/188,971, filed on Nov. 10, 1998, now Pat. No. 6,248,064, which is a continuation-in-part of application No. 09/084,647, filed on May 26, 1998, now Pat. No. 6,224,548, said application No. 09/741,283 is a continuation of application No. 09/084,647, filed on May 26, 1998, now Pat. No. 6,224,548.

(51) Int. Cl.
*G06Q 10/00* (2012.01)

(52) U.S. Cl. ................................. 705/2; 705/3; 600/300
(58) Field of Classification Search .................. 705/2, 3; 600/300

See application file for complete search history.

(56) References Cited

U.S. PATENT DOCUMENTS 206,474 A 7/1878 Morel
(Continued)

FOREIGN PATENT DOCUMENTS

EP 0459239 A2 12/1991
(Continued)

OTHER PUBLICATIONS

Wyman, Gail, "The Maturing of Telemedicine Technology", Sep./Oct. 1994, vol. 27, Iss. 5, p. 57.
(Continued)

*Primary Examiner* — Lena Najarian
(74) *Attorney, Agent, or Firm* — Brooks Kushman P.C.

(57) ABSTRACT

A method for remote medical consulting includes collecting diagnostic data using at least one wearable device contoured to at least a portion of a person's hand, transmitting the diagnostic data to a remote location, transmitting audio data and video images of the patient to the remote location, and communicating diagnosis and/or treatment information to the patient based at least in part on the diagnostic data. The treatment information may include a prescription electronically transmitted to the patient or a pharmacy. The method includes billing of the patient via credit or debit card, bank account, or a third party, such as an insurance company. The diagnostic data as well as the audio and video data may be transmitted wirelessly via cellular or satellite communication networks and/or using a wide area computer network such as the internet.

35 Claims, 3 Drawing Sheets

U.S. PATENT DOCUMENTS

| | | | |
|---|---|---|---|
| 3,888,240 A | | 6/1975 | Reinhold, Jr. et al. |
| 4,016,868 A | * | 4/1977 | Allison .................. 600/388 |
| 4,230,127 A | | 10/1980 | Larson |
| 4,381,012 A | | 4/1983 | Russek |
| 4,510,939 A | | 4/1985 | Brenman et al. |
| 4,556,063 A | | 12/1985 | Thompson et al. |
| 4,583,547 A | | 4/1986 | Granek et al. |
| 4,608,987 A | | 9/1986 | Mills |
| 4,662,378 A | | 5/1987 | Thomis |
| 4,698,848 A | | 10/1987 | Buckley |
| 4,709,704 A | | 12/1987 | Lukasiewicz |
| 4,974,607 A | | 12/1990 | Miwa |
| 5,007,427 A | | 4/1991 | Suzuki et al. |
| 5,224,479 A | | 7/1993 | Sekine |
| 5,353,793 A | | 10/1994 | Bornn |
| 5,431,170 A | | 7/1995 | Mathews |
| 5,441,047 A | * | 8/1995 | David et al. ............. 600/483 |
| 5,442,729 A | | 8/1995 | Kramer et al. |
| 5,465,727 A | | 11/1995 | Reinhold, Jr. |
| 5,511,546 A | | 4/1996 | Hon |
| 5,564,429 A | | 10/1996 | Bornn et al. |
| 5,619,991 A | | 4/1997 | Sloane |
| 5,626,151 A | | 5/1997 | Linden |
| 5,640,953 A | | 6/1997 | Bishop et al. |
| 5,666,404 A | | 9/1997 | Ciccotelli et al. |
| 5,670,944 A | | 9/1997 | Myllymaki |
| 5,687,738 A | | 11/1997 | Shapiro et al. |
| 5,701,904 A | | 12/1997 | Simmons et al. |
| 5,704,364 A | | 1/1998 | Salzstein et al. |
| 5,730,140 A | | 3/1998 | Fitch |
| 5,738,104 A | | 4/1998 | Lo et al. |
| 5,758,095 A | | 5/1998 | Albaum et al. |
| 5,771,001 A | | 6/1998 | Cobb |
| 5,771,891 A | | 6/1998 | Gozani |
| 5,785,650 A | | 7/1998 | Akasaka et al. |
| 5,787,650 A | | 8/1998 | Miller et al. |
| 5,855,550 A | | 1/1999 | Lai et al. |
| 5,877,675 A | | 3/1999 | Rebstock |
| 5,902,234 A | | 5/1999 | Webb |
| 5,906,582 A | | 5/1999 | Kondo et al. |
| 5,964,701 A | | 10/1999 | Asada et al. |
| 5,967,559 A | | 10/1999 | Abramowitz |
| 5,994,701 A | | 11/1999 | Tsuchimoto et al. |
| 6,022,321 A | | 2/2000 | Anamo et al. |
| 6,078,907 A | * | 6/2000 | Lamm ......................... 705/40 |
| 6,217,523 B1 | | 4/2001 | Amano et al. |
| 6,224,548 B1 | | 5/2001 | Gopinathan et al. |
| 6,248,064 B1 | | 6/2001 | Gopinathan et al. |
| 6,285,991 B1 | | 9/2001 | Powar |
| 6,319,205 B1 | | 11/2001 | Goor et al. |
| 6,322,515 B1 | | 11/2001 | Goor et al. |
| 6,726,638 B2 | * | 4/2004 | Ombrellaro .............. 600/587 |
| 6,961,448 B2 | | 11/2005 | Nichols et al. |
| 7,860,725 B2 | | 12/2010 | Gopinathan et al. |

FOREIGN PATENT DOCUMENTS

| | | |
|---|---|---|
| EP | 0706776 A1 | 4/1996 |
| EP | 0761160 A1 | 3/1997 |
| EP | 0770349 A1 | 5/1997 |
| EP | 0880936 A2 | 12/1998 |
| WO | 8402459 A1 | 7/1984 |
| WO | 9804182 A2 | 2/1998 |
| WO | 9817172 A2 | 4/1998 |

OTHER PUBLICATIONS

Fishman, Dorthy J., "Telemediine: Bringing the Specialist to the Patient", Chicago: Jul. 1997, vol. 28, Iss. 7, p. 30.

Kiernan, Vincent, "Computers you can put on may soon be no put-on", Chronicle of Higher Education (GCHE), V. 44, n9., Oct. 24, 1997.

Kiernan, Vincent, "Computers You Can Put on May Soon Be No Put-On", The Chronicle of Higher Education, Oct. 24, 1997 A21-22.

Murakami Hajime et al., "Telemedicine Using Mobile Satellite Communication", XP-000770263, IEEE Transactions on Biomedical Engineeering, vol. 41, No. 5, May 1994, pp. 488-497.

* cited by examiner

METHOD FOR REMOTE MEDICAL CONSULTATION AND CARE

CROSS-REFERENCE TO RELATED APPLICATIONS

This application is a continuation of U.S. application Ser. No. 10/310,334 filed Dec. 5, 2002, now U.S. Pat. No. 7,860,725, issued on Dec. 28, 2010, which is a continuation-in-part of U.S. patent application Ser. No. 09/884,371, filed Jun. 19, 2001, now U.S. Pat. No. 6,595,918, issued on Jul. 22, 2003, and 09/741,283, filed Dec. 19, 2000, now U.S. Pat. No. 6,540,673, issued on Apr. 1, 2003. U.S. patent application Ser. No. 09/884,371, filed Jun. 19, 2001 is a continuation of U.S. patent application Ser. No. 09/188,971, filed Nov. 10, 1998, now U.S. Pat. No. 6,248,064, issued on Jun. 19, 2001, which is a continuation-in-part of U.S. patent application Ser. No. 09/084,647, filed May 26, 1998, now U.S. Pat. No. 6,224,548, issued on May 1, 2001. U.S. patent application Ser. No. 09/741,283 is a continuation of U.S. patent application Ser. No. 09/084,647, filed May 26, 1998, now U.S. Pat. No. 6,224,548, issued May 1, 2001. These applications are incorporated hereby by reference in their entirety.

TECHNICAL FIELD

The present invention relates to a method for remote medical consultation and patient care.

BACKGROUND

Telemedicine, providing medical consultation, testing, and advice over electronic communication pathways to people at locations remote from the medical personnel providing the care has been in development. However, most doctors and patients have been reluctant to depend on telecommunication and computer technology to perform such an important role in medical care having potential life or death consequences. Traditional medical training teaches that a good doctor should interrogate the patient face-to-face, examine the patient personally, and discuss diagnostic and treatment considerations, again, face-to-face. Those who can still remember reminisce about the days when doctors had the availability to make house calls and spend considerable time with each patient to establish a personal relationship over the course of many years. As increasing demands have been placed on both doctors and patients, the paradigm for medical care has evolved to require patients to travel to seek medical care. In an effort to control costs, patients are encouraged or required to seek the least expensive care for their condition. However, patients typically are not qualified to diagnose their own medical condition and determine an appropriate medical professional for treatment, whether a nurse, nurse practitioner, physician assistant, physician, specialist, etc. Even if the patients properly diagnose a medical condition, or properly determine that specialty care is needed, those who participate in a managed care plan typically are required to visit their general practitioner or primary care physician for a diagnosis and referral for specialized care. Each visit may require waiting several days or weeks to schedule an appointment, traveling to a different office or medical center, completing additional paperwork (by the patient and physician), and waiting on the day of the appointment at the point of service, all of which takes time from otherwise productive activities.

The rapid and spectacular developments in telecommunication and computer technologies have brought countries and continents closer and closer together. With all of the available conveniences, people are reluctant to wait for anything. The need to communicate instantly with friends, relatives, and business associates, irrespective of location has become the order of the day. Cellular phones, and more recently satellite phones, are so commonplace that they are considered part and parcel of daily life. However, in spite of the availability of this technology, it still remains a difficult and ill-structured task to consult with a doctor when one is needed, especially when away from home or out of town. Patients often must travel significant distances, rearrange schedules, and make other accommodations and concessions and to seek care. As such, many patients may not seek care soon enough for optimal treatment, and/or may forgo follow-up care.

While some prior art telemedicine strategies have attempted to overcome one or more of the problems identified above, none have used sufficiently sophisticated, yet user-friendly and easy to use diagnostic/treatment tools, in combination with integrated audio and video to make both physicians and patients comfortable with delivering medical care remotely.

SUMMARY

A method for implementing a virtual face-to-face medical consultation according to the present invention utilizes a simple and easy-to-use, compact, light weight, portable and affordable diagnostic unit capable of generating and transmitting vital bio-data to a distant location where it is interpreted by a medical professional or a medical facility, in many instances with emergency medical personnel. In one embodiment, the method uses a device having a wearable form factor, such as one or two gloves, to generate multi-sensor diagnostic bio-data and/or deliver emergency treatment to a remotely located patient. The data generated by the multi-sensor device is conveyed through a multi-conductor cable to an electronic transmission box containing a compact, consolidated circuit board unifying various processing circuitry to condition and transmit signals for EKG, oxygen saturation, blood pressure, pulse, temperature, and two-way audio and video. The transmission box is capable of transferring a combined data stream over a wide area network, which may include a proprietary network, or the internet, for example. Patient care may be immediately administered as needed using the wearable sensor/treatment device, and/or through direct audio/video communication with the patient, local bystanders, and/or emergency medical personnel. For non-emergency treatment, one or more prescriptions may be ordered by the physician directly via the wide area network and subsequently delivered to the patient by mail or courier. The method also preferably includes the ability to electronically process patient billing and payment information either directly using a credit/debit card or checking account, or via a third-party, such as an insurance company or government program.

More specifically, in one embodiment of a method for remote medical consulting between a patient and medical personnel according to the present invention, the method includes collecting identification information from the patient, preferably electronically using a bar code or by reading an implanted electronic device, for example. Diagnostic data is collected using at least one wearable device contoured to at least a portion of a person's hand. The wearable device includes a plurality of diagnostic devices for generating signals in response to corresponding body characteristics of the patient. The method further includes transmitting the diagnostic data generated using the wearable device to a remote location, transmitting audio data and video images of the patient to the remote location, and communicating diagnosis and/or treatment information to the patient based at least in part on the diagnostic data. The treatment information may include a prescription electronically transmitted to the patient or a pharmacy. In addition, integrated billing of the patient or a third party, such as an insurance company, is also provided. The diagnostic data as well as the audio and video data may be transmitted wirelessly via cellular or satellite communication networks and/or using a wide area computer network such as the internet.

The present invention provides a number of advantages. For example, instead of a patient traveling to see a doctor, the doctor can virtually come to the patient and maintain a face-to-face relationship even if cities, countries, or continents separate them. The real-time, virtual face-to-face medical consultations (and/or treatment) at the convenience of the patient eliminate travel time and substantially reduce or eliminate waiting time, while allowing medical professionals to maintain the highest quality and dedication to the principles of medical care. The availability of online knowledge bases for diagnosis and treatment of less common maladies provides for the highest level of care as taught and practiced at the finest medical centers. The increased efficiency of the remote consultation method of the present invention affords significant opportunities for cost reduction in the delivery of routine medical services. Integrated prescription processing and electronic billing and payment are convenient for patients and reduce paperwork for physicians. In addition, the present invention is suitable for remote monitoring and emergency medical intervention, particularly for home health care and long-term care scenarios that will continue to increase as the "baby-boom" generation ages. The method provides a personal physician to homes, workplaces, and many other sites effectively delivering medical services to anyone, anywhere, and at anytime.

A steadily increasing trend in medical care substitutes lesser-trained medical practitioners for the delivery of various health services. However, the method according to the present invention actually allows increased doctor-patient contact while facilitating cost reductions by increasing physician productivity. In addition, bringing the doctor to the patient should increase patient compliance with follow-up care. While there may always be a need for office visits, the method of the present invention allows effective screening of many routine visits that can be accommodated just as easily, and at a reduced cost, at the patient's home or office.

The present invention may also reduce the physician's cost of doing business by reducing the need for expensive office space and staff at multiple locations, without degrading the physician's role, or quality of care. In addition, the method provides a cost-effective alternative to provide high-quality medical care to locations usually bereft of physician-level care, such as on ships and airplanes, in large arenas, and at remote or isolated destinations. Furthermore, the method provides continuity of care by allowing those traveling to be diagnosed and treated by their own physician or physician's group who is familiar with the patient and family medical history rather than by a locally available physician that may not be aware of relevant information, and may not be available for additional follow-up care.

The wearable diagnostic/treatment device used in the present invention delivers patient bio-data to a remotely located physician. The audio capabilities allow the doctor to listen to the patient's heart, lungs, or abdomen in addition to providing two-way conversation between the doctor and patient. Real-time video provides the doctor with images of the patient while allowing the patient to visualize the doctor, giving the sense of a face-to-face consultation. The patient can provide video of any part of the body helpful to the diagnosis or treatment as guided by the doctor. Video images can be saved and stored in the patient's electronic record for future reference, such as documenting changes during a course of treatment.

The wearable sensor used in one embodiment for virtual medical consultations can also be used during a traditional office visit to improve efficiency. When the patient arrives in the doctor's office, he or she could proceed to a pre-screening room to use the wearable diagnostic device to generate current bio-data for use by the physician during the visit. The generated data can be immediately delivered to the doctor's PC or other computing device for review with relevant data being electronically stored in the patient's file for future reference. For patient's willing to purchase the wearable diagnostic/treatment device, the patient can participate in a virtual fact-to-face full consultation with the doctor from the comfort of her home. The time savings alone, particularly for those who must contend with urban traffic, parking, or other transportation, can quickly justify the cost of the device for an individual or family.

The virtual face-to-face medical consultations according to the present invention also avoid exposing patients who may already have a compromised immune response due to their own illness to pathogens carried by other patients.

Because of the inconvenience associated with a typical office visit, patients (or their parents) may pressure the doctor to prescribe antibiotics even though there is no clear medical indication of a bacterial infection to avoid the necessity of another visit if the condition does not quickly improve. The increased availability and convenience of a virtual medical consultation according to the present invention may make repeated consultations more palatable when needed and reduce the dispensing of unnecessary antibiotics, and the related development of resistant strains of bacteria.

The above advantages and other advantages, objects, and features of the present invention, will be readily apparent from the following detailed description of the best mode for carrying out the invention when taken in connection with the accompanying drawings.

DETAILED DESCRIPTION OF THE PREFERRED EMBODIMENT(S)

Figure 1:
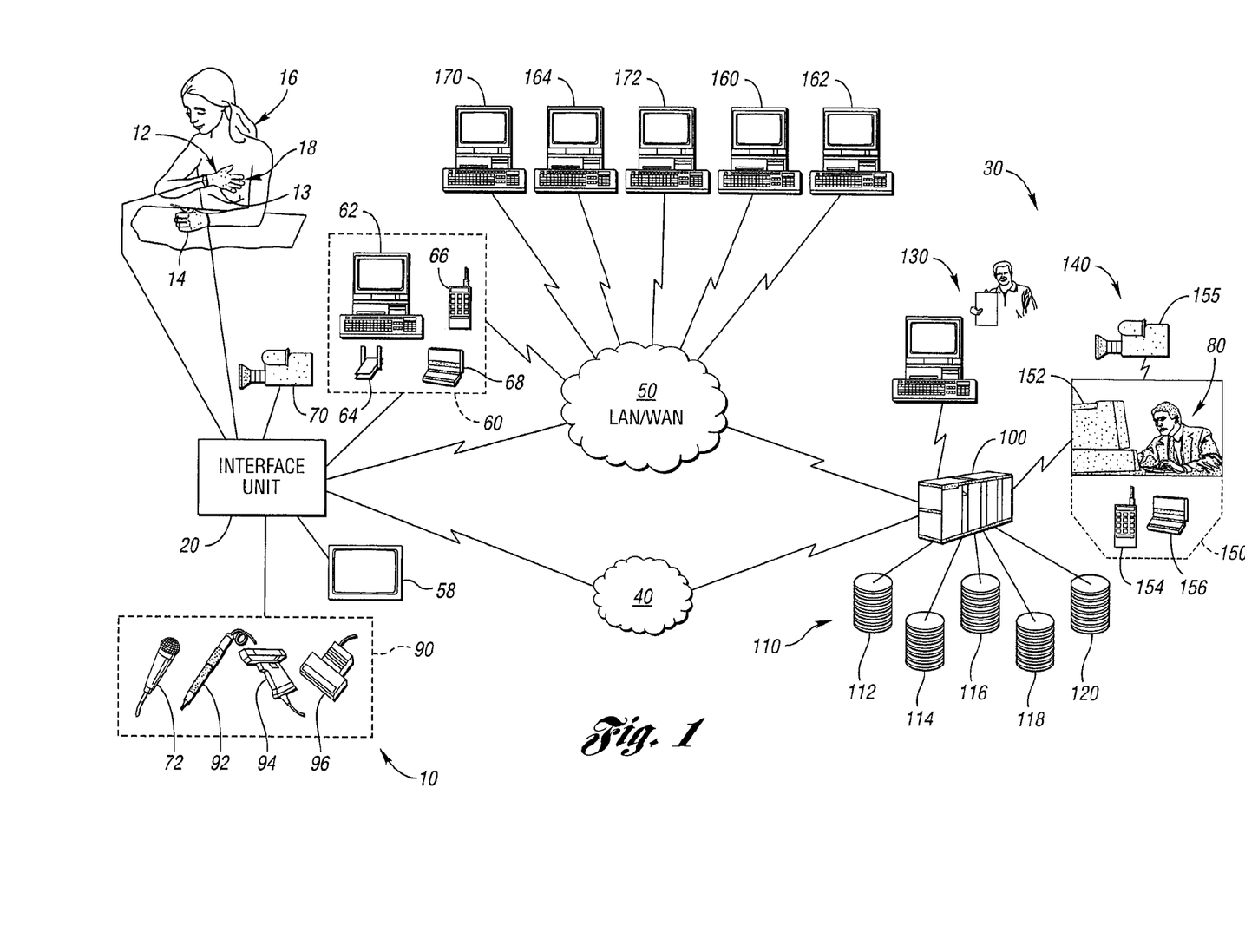
FIG. 1 is a block diagram illustrating operation of a method for medical consultation according to one embodiment of the present invention.

Referring now to FIG. 1, a graphical representation illustrates one embodiment of a method for medical consultation or interaction between medical personnel and a patient or caregiver according to the present invention. As will be appreciated by those of ordinary skill in the art, the present invention encompasses various types of remote medical care, interaction, consultation, therapy, etc. that may be provided directly to a patient or indirectly through a local caregiver, such as a friend, relative, nurse, technician, or other personnel. The medical care or interaction may include but is not limited to medical advice for treatment or referral for additional care, prescribing medication, and/or direct or indirect remote actuation of therapeutic devices to deliver routine or emergency medical treatment, for example. The method illustrated in FIG. 1 for implementing a virtual face-to-face medical consultation according to the present invention utilizes a simple and easy-to-use, compact, light weight, portable and affordable diagnostic unit indicated generally by reference numeral 10. In this embodiment, diagnostic unit 10 includes an interface unit 20 and at least one wearable device 12 capable of collecting diagnostic data from at least one integrated diagnostic device or sensor. The wearable device 12 includes one or more sensors or diagnostic devices that generate signals in response to corresponding body characteristics of a patient 16 when positioned over appropriate portions 18 of the patient's body. The wearable device 12 preferably generates signals indicative of pulse rate, blood pressure, and temperature of patient 16. In addition, an auscultation device incorporating a microphone for capturing body sounds may be integrated within wearable device 12 and/or diagnostic unit 10. Wearable diagnostic device 12 may also provide signals for determining blood oxygen saturation and a multiple lead EKG, in addition to providing treatment transducers for cardiac defibrillation or other treatment as described in detail in U.S. Pat. Nos. 6,224,548 and 6,248,064, the disclosures of which are hereby incorporated by reference in their entirety.

In the embodiment illustrated in FIG. 1, wearable device 12 includes two gloves 13, 14 that can be placed on respective hands of patient 16 or someone other than patient 16 depending upon the particular application. Wearable device 12 is removably connected, in this embodiment via a multiconductor cable, to an interface unit 20, illustrated and described in greater detail with reference to FIG. 2. In general, interface unit 20 contains a compact, consolidated circuit board unifying various processing circuitry to condition signals received from wearable device 12 for local display of corresponding information and/or direct or indirect transmission of the diagnostic data to a remote location, indicated generally by reference numeral 30.

For direct transmission, interface unit 20 may include a modem to securely transmit diagnostic information over a conventional packet switched telephone network (PSTN) 40, a cellular network, or via satellite. Alternatively, or in addition, interface unit 20 may include an appropriate computer network interface to securely transmit and receive information directly over a local or wide area computer network 50, which may include a proprietary network or a publicly available global network such as the internet, for example. Preferably, a secure transmission protocol is used to ensure privacy and to provide a guaranteed quality of service for transmitting the diagnostic data. Depending upon the available transmission modes, bandwidth, and current level of telephone/computer network traffic, interface unit 20 may use more than one transmission mode/medium for various types of data during a particular consultation, or may select a particular transmission mode prior to beginning transmission of diagnostic data, as explained in greater detail with reference to FIG. 2.

As also illustrated in FIG. 1, interface unit 20 may transmit diagnostic data indirectly via one or more local network devices 60. The communication link between interface unit 20 and one or more network devices 60 may be wired or wireless. For example, interface unit 20 may communicate with a desktop or laptop computer 62 via a cable or wirelessly via a local access point 64. Computer 62 may provide some processing of signals from interface unit 20 for local display of diagnostic information for viewing by patient 16 or others. Alternatively, or in combination, a dedicated diagnostic display 58 may be used to display diagnostic information. Dedicated display 58 or computer 62 may also provide temporary or permanent storage of raw data or processed information for subsequent retrieval by patient 16 or others. Computer 62 can then transmit diagnostic data over local and/or wide area network 50 to remote location 30 using any of a number of available transmission modes, such as via telephone or cable modem, digital subscriber loop (DSL), satellite, etc.

Interface unit 20 may also communicate via a wired or wireless link with a network enabled cellular telephone 66. In one embodiment, interface unit 20 is miniaturized to the size of a subscriber identity module (SIM) card and adapted for insertion into mobile telephone 66, which is then used to transmit the diagnostic data to any location in the world, represented by remote location 30. Mobile telephone 66 may be a conventional cellular telephone with local wireless access, or alternatively a dual mode or tri-mode phone with both conventional analog/digital (AMPS, CDMA, or GSM) and satellite access for worldwide coverage, such as the Globalstar mobile phones available from Qualcomm, Inc. of San Diego, Calif. or Ericsson, Inc. of Plano, Tex., for example. Mobile phone 66 may also incorporate positioning functions using the global positioning system (GPS), such as the NavTalk mobile phone available from Garmin International, Inc. of Olathe, Kans. Similarly, a handheld computing device 68, such as a handheld computer or personal digital assistant (PDA) may be used to provide wireless access to network 50 using cellular and/or satellite communication links with an integrated antenna or via a wired connection to a mobile phone 66 or other communication device.

Diagnostic unit 10 preferably includes a camera 70 to provide a video image of patient 16. Camera 70 may provide still images but is preferably capable of image capture rates of 30 frames per second (fps) to provide full motion video. The frame rate may be adjusted depending upon the particular application and the currently available communication devices and telephone or computer network bandwidth and quality of service. The frame rate may vary during a particular consultation in combination with increased or decreased resolution based on the current use of camera 70. For example, a higher frame rate and lower resolution may be used for general conversation between patient 16 and medical personnel 80 at remote location 30, while a higher resolution and lower frame rate or still picture may be used to provide a more detailed image or close-up of body portion 18 to provide a more thorough visual examination. Depending upon the particular application, camera 70 may also include various remotely controllable features to facilitate visual examination by medical personnel 80. For example, camera 70 may include remotely controllable pan, zoom, and tilt controls that can be operated from remote location 30. Camera 70 also preferably includes local controls for operation by patient 16 or others in response to requests or instructions from medical personnel 80. Camera 70 is preferably connected via a wired or wireless communication link to interface unit 20 which may include appropriate video processing and compression electronics and software. Alternatively, camera 70 may be connected to or integrated with local network device(s) 60, which may include video processing hardware and/or software to process and/or store one or more video images.

Diagnostic unit 10 preferably includes at least one microphone 72 to provide an audio link from patient 16 or local surroundings. Microphone 72 may be integrated into wearable device 12, interface unit 20, camera 70, or network device(s) 60. Depending upon the particular application, microphone 72 may be linked via wireless or wired connection to interface unit 20 or to local network device(s) 60, which preferably include temporary and permanent storage capabilities to store audio and video information associated with a particular consultation for subsequent retrieval. The capability to store and subsequently retrieve audio and/or video information is a valuable resource for medical personnel to compare diagnostic data over time for the assessment of a progressive illness or in evaluating the effectiveness of a course of treatment, for example. Representative audio information may include body sounds captured by auscultation device integrated into wearable device 12, such as heart, lung, or abdominal sounds. Audio information may also include verbal explanations or instructions given by medical personnel 80 that may be subsequently retrieved for review by patient 16.

As will be appreciated by those of ordinary skill in the art, although illustrated as a separate component in FIG. 1, interface unit 20 may be directly connected or integrated into wearable device 12 with diagnostic data transmitted wirelessly either directly or indirectly over network 50 as described above. Likewise, interface unit 20 may be plugged into or otherwise directly connected to local network device (s) 60. The method of the present invention is independent of the particular form factor of interface unit 20, although it should embody characteristics to make wearable device 12 relatively convenient, light weight, and generally easy to use for typical patients.

Depending upon the particular application, the method of the present invention may utilize various auxiliary input devices 90 to quickly, conveniently, and uniquely identify a conscious or unconscious patient for the medical consultation, which may include emergency treatment as described above. Auxiliary input devices 90 may include an optical scanner 92 that can be used to read single or multidimensional bar code information, such as may be included on a medical alert bracelet or other identification worn by patient 16. Optical scanner 92 may also be suitable for high resolution scanning, such as used for retinal scanning and identification. Alternatively, camera 70 may capture bar code information or other optical identification information to uniquely identify patient 16. Auxiliary input devices 90 may also include a magnetic strip reader 94 to read encoded information on a credit card, driver's license, insurance card, or other identification, payment, or medical information for patient 16. Similarly, an electronic device reader 96 may be provided to read information from an identification or other device implanted in patient 16. For example, patients experiencing various forms of confusion or dementia, such as sometimes associated with Alzheimer's disease and many others, may be equipped with wearable or implanted devices incorporating GPS devices to locate the patient and encoded identification and medical information that may be accessed by reader 96, such as the VeriChip or Digital Angel products available from Applied Digital Solutions of Palm Beach, Fla. Likewise, children or travelers may also don such electronic devices for easy identification using an electronic device reader. Other implanted medical devices, such as pace makers and automatic defibrillators may also contain information that can be used to uniquely identify the patient, and may include a brief medical history, allergies, etc. Of course, patients could also provide identification and medical information using a combination of manual and automatic or voice recognition or response systems. For example, a computer keyboard, telephone keypad, or PDA could be used to enter a name or identification number. Likewise, a voice recognition system could be used to convert or transcribe voice data to corresponding alphanumerical data. Likewise, a voice print or other biometric data may be used to identify the patient. Once identified, various patient-related information for established patients can be easily retrieved including medical history, allergies, payment arrangements or insurance information, etc. as described in greater detail below.

Diagnostic data gathered by diagnostic unit 10, which may include video and audio information, is transmitted to remote location 30 via telephone/satellite network 40 or local/wide area computer network (LAN/WAN) 50. Remote location 30 (or an intermediate command center) includes one or more computers 100 containing hardware and/or software to facilitate virtual face-to-face medical consultations according to the present invention. The hardware/software associate with computer 100 performs various tasks utilizing one or more programmed microprocessors and related temporary and permanent computer readable storage media, generally represented by reference numeral 110. Computer readable storage media 110 may include various programs, modules, databases, and the like to perform consultation routing and scheduling functions 112, billing and payment functions 114, and patient medical history storage and retrieval functions 116. A local knowledge base 118 may also be provided for use by medical personnel 80 to provide diagnosis and treatment advice. Computer 100 may also be used to control bio-data adjustment software/hardware 120, which is used to provide medical personnel 80 with flexibility in calibrating or correcting sensor output from diagnostic unit 10. This provides one layer of back-up or redundancy that is incorporated into the consultation system. Routing/scheduling module of computer 100 may perform a triage function of routing consultation requests by urgency with emergency requests routed to an appropriate emergency response center 130 and scheduling routine or follow-up consultations via one or more virtual offices 140. Emergency response center 130 and virtual offices 140 may contain one or more network devices 150 in communication with computer 100 via wired or wireless communication links as described with reference to local network devices 60. Similarly, network devices 150 may include a desktop or laptop computer 152, mobile phone 154, camera 155 or handheld computer or PDA 156.

Scheduling module 112 facilitates routine administrative tasks such as establishing new patients and obtaining biographical information, family history, medical history, and payment or insurance information. Payment information may include direct payment by the patient via a credit/debit card or electronic transfer from a banking account (checking, savings, money market, etc.), for example. Scheduling module 112 provides patients with significant flexibility in scheduling routine consultations by allowing the patient to view available appointment days and times and can reduce the administrative burden for medical personnel 80 as well.

Billing processing module 114 includes the ability to verify credit/debit card account numbers for accuracy when established or changed by a patient. This module may also include insurance billing requirements including covered and uncovered diagnoses, treatments, and prescriptions, for example. Preferably, billing processing module 114 processes charges for online consultations and directly bills the responsible party based on the patient identification information with the ability to electronically receive payment from a corresponding credit/debit card issuer 160, insurance company 162, or financial institution 164 via telephone network 40 or computer network 50.

Patient medical history module 116 may be used to store a wealth of information that may be used by medical personnel 80 for diagnosis and treatment of patient 16 relative to an online medical consultation. The medical history information may be retrieved almost instantly using the patient identification information and may include stored video information, both still photos and full-motion video, of previous diagnostic tests or consultations. For example, images captured from endoscopic studies, such as a colonoscopy or gastroscopy, radiological studies, such as CT scans, MRI scans, etc., or photographs of skin conditions, etc. can be stored and subsequently retrieved for a particular patient. Audio information, such as heart sounds, lung sounds, etc. may also be digitally stored and subsequently retrieved by medical history module 116.

Local knowledge base 118 provides a valuable resource for medical practitioners 80 for diagnosis and treatment based on patient diagnostic data captured using diagnostic unit 10. Local knowledge base 118 may be any of a number of commercially available or proprietary systems used to assist in diagnosing various illnesses and providing recommended treatment regimens. In addition, computer 100 has the ability to access one or more remotely located resources, represented generally by remote knowledge base 170, via computer network 50 for specialty care. This effectively provides patient 16 with the most up-to-date and best available medical care from a variety of medical research centers without having to schedule multiple office visits and travel to multiple distant locations.

As also illustrated in FIG. 1, computer 100 preferably includes a communication link to various pharmacies 172 via telephone network 40 and/or computer network 50. According to the present invention, medical practitioners 80 may electronically prescribe medication for treatment of patient 16. The electronic prescription may be transmitted directly to a pharmacy 172 for dispensing as specified by patient 16 and/or previously associated with a patient profile by patient history module 116. Alternatively, an electronic prescription may be transmitted to patient 16 for manual delivery to a local pharmacy. Appropriate validation of a printed prescription may be provided by a variety of systems, such as two-dimensional bar codes, to verify the authenticity of the prescription. Prescription information may be electronically exchanged between pharmacy 172 and the medical practitioner issuing the prescription as stored in the patient profile to ensure authenticity and monitor compliance. Depending upon the type of medication and the urgency with which it should be delivered, pharmacy 172 may deliver the medication to patient 16 by mail, courier, or hand delivery. For prescription refills or long-term therapy, a pharmacy may be selected based on lowest cost for a particular medication without regard to the distance of the pharmacy from patient 16 with delivery by mail or courier service.

Figure 2:
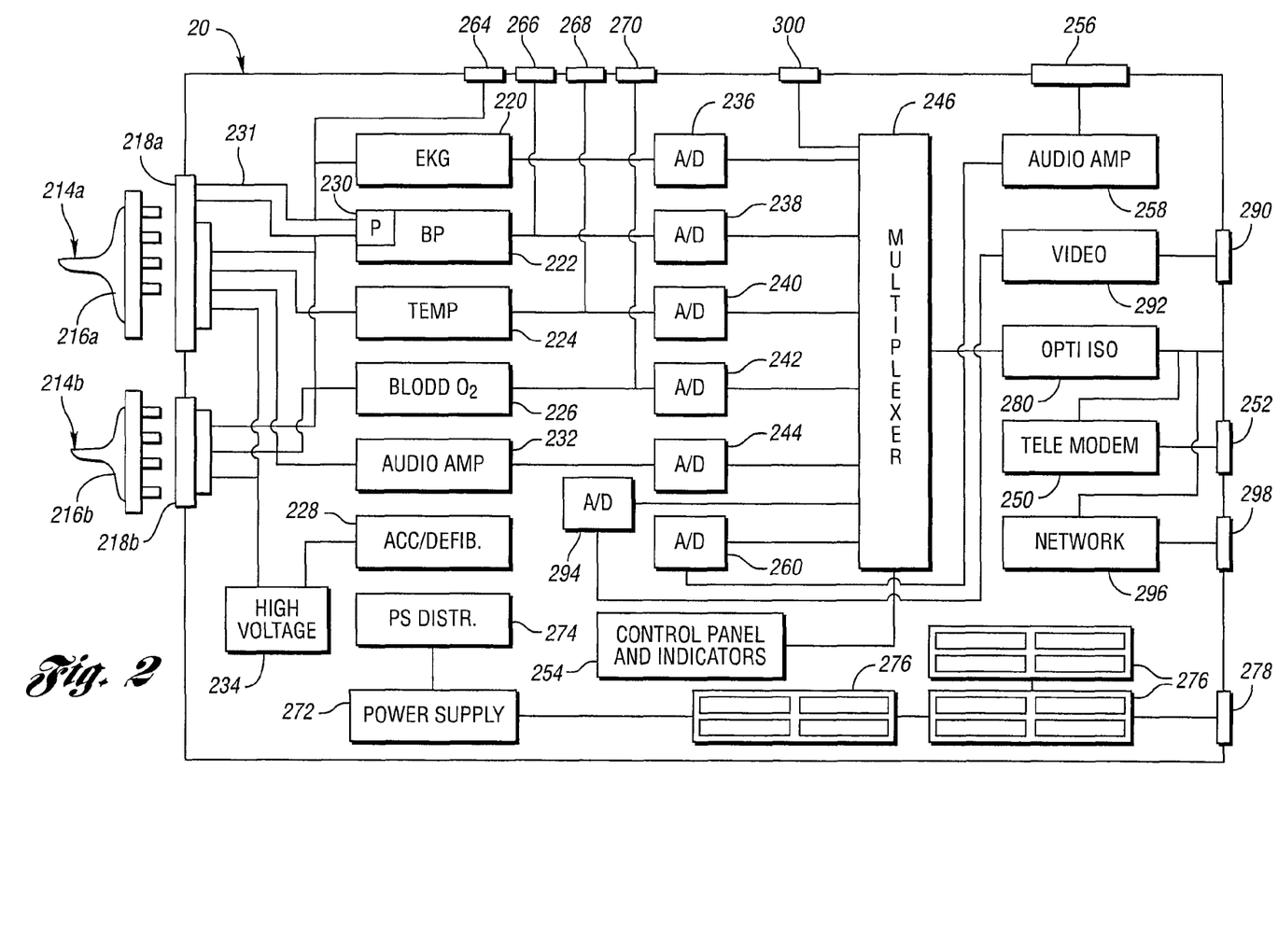
FIG. 2 is a block diagram illustrating additional details of an interface unit for use in a method for medical consultation according to one embodiment of the present invention.

Referring now to FIG. 2, a block diagram illustrates internal components for a representative embodiment of an interface unit 20 used in a method for remote medical consultations according to the present invention. Depending upon the particular implementation, interface unit 20 may be integrated into wearable device 12 or may be a separate component with an appropriate connector, such as connector 216a and receiver plug 218a, to electrically couple the wearable device via multi-conductor cable 214a. A mechanical interlock or retainer (not shown) may also be provided to enhance the reliability of the connection and inhibit accidental disconnection during use. Depending upon the particular application, a wearable device 12 may include a second glove connected via corresponding cable 214b, connector 216b and receiver 218b. One or both multiconductor cables 214a, 214b include a plurality of electrical conductors and may include one or more fluid conduits to provide electrical, audio, and fluid communication between wearable device 12 and interface unit 20.

Depending upon the particular application, interface unit 20 may include EKG signal processing logic and/or circuitry 220 for receiving EKG currents detected by corresponding sensors on wearable device 12 (FIG. 1), blood pressure signal processing logic and/or circuitry 222 for receiving systolic and diastolic blood pressure and pulse rate signals, temperature signal processing logic and/or circuitry 224 for receiving temperature signals, blood oxygen saturation processing logic and/or circuitry 226 for receiving corresponding signals and acupuncture/defibrillator circuitry and/or logic 228 for controlling delivery of a therapeutic electrical shock to the patient.

As will be appreciated by those of ordinary skill in the art, the various signal conditioning, processing, and/or control functions may be implemented solely using electronic circuitry using various fabrication techniques depending upon the desired form factor, manufacturing costs, and various other considerations. However, these functions may also be performed by electronic circuitry in combination with one or more embedded microcontrollers and/or microprocessors having encoded logic and instructions stored in associated non-volatile memory to provide increased performance and flexibility while facilitating periodic enhancements or upgrades. The present invention is independent of the particular implementation of the signal conditioning or processing circuitry but contemplates a unified, composite circuit board implementation such that the form factor is suitable for insertion into a network device, such as a mobile telephone or computer.

EKG processor 220 is capable of amplifying the corresponding signal currents received from wearable device 12 and converting the EKG currents to a plurality of EKG analog outputs. The EKG circuitry 220 may include various components similar, or identical, to parts of the PC-ECG recorder unit from I.P.I. Medical Products of McLean, Va.

Blood pressure circuitry 222 is capable of converting systolic and diastolic blood pressure signals to corresponding analog outputs and converting pulse rate signals to a pulse rate analog output. Blood pressure circuitry 222 includes a source of inflation fluid, such as an air pump 230 for supplying a source of inflation fluid for an air bladder contained in wearable device 12, and an acoustical sensor (not shown) for detecting the systolic and diastolic blood pressure and pulse rate signals. Air pump 230 is in fluid communication with the air bladder via the fluid conduit in cable 214a and air conduit 231, which extends between and provides fluid communication between female connection plug 218a of the interface unit 20 and air pump 230. Blood pressure circuit board 222 may contain various components similar, or identical, to parts of the UB-302 Systolic/Diastolic (Pulse) Digital Blood Pressure monitor from A+D Engineering Inc., of Milpitas, Calif.

Temperature circuitry 224 is capable of converting the temperature signals to a temperature analog output and may include various components similar, or identical, to parts of the Cole-Parmer E-08402-00 digital thermometer from Cole-Parmer, of Vernon Hills, Ill. The blood oxygen saturation circuitry 226 is capable of converting signals from wearable device 12 to a corresponding analog output. Circuitry 226 may include one or more components similar, or identical to components found on the Nonin Onyx blood flow and oxygen saturation reader, model No. 8500M from Nonin Medical, Inc., of Plymouth, Minn. Interface unit 20 also includes a first audio amp 232 for amplifying sound waves received from an auscultation device integrated into wearable device 12. Acupuncture defibrillator circuitry 228 selectively regulates the amount of electrical energy supplied by the defibrillator device and the acupuncture device of wearable device 12. A high voltage source 234 is contained within interface unit 20 to supply power to electrodes on wearable device 12 to deliver an electrical shock to the patient when needed as determined by local or remote medical personnel.

Interface unit 20 further includes a first analog to digital (A/D) converter 236 for converting EKG analog outputs to an EKG digital data stream, a second A/D converter 238 for converting the systolic and diastolic blood pressure analog outputs and the pulse rate analog output to corresponding digital data streams, a third A/D converter 240 for converting the temperature analog output to a temperature digital data stream, a fourth A/D converter 242 for converting the percent oxygen analog output to a percent oxygen digital data stream, and a fifth A/D converter 244 for converting analog signals from the first audio amp 232 to a corresponding digital data stream. Interface unit 20 may also include an integrated speaker/microphone 256, associated audio amp 258, and a sixth analog to digital converter 260 to enable a medical professional in the remote location 30 (FIG. 1) to communicate orally with the persons in relative close proximity to speaker/microphone 256. Alternatively an external speaker/microphone may be connected via a corresponding port (not shown), or a network device 60 (FIG. 1) may include an integrated or external speaker and microphone.

Of course, depending upon the particular implementation, one or more of the input devices or the integrated signal processing/conditioning modules may produce a digital data stream and would not require a separate A/D converter as illustrated in FIG. 2. For example, an analog video camera may be connected via port 290 with its signal processed by video capture and processing circuitry 292 before being provided to A/D converter 294. Alternatively, a digital video camera or other digital input device may be connected via one or more digital input ports 300 such that the digital input stream bypasses the A/D converters.

Interface unit 20 includes a multiplexer 246 for combining the digital data streams from the analog to digital converters and digital input ports to form a combined digital data stream. The combined digital data stream can then be conveyed to a local control panel and indicator circuitry 254 in addition to being transmitted directly or indirectly to remote location 30 (FIG. 1) via modem 250 and corresponding port 252 and/or via network interface 296 and corresponding port 298 as previously described. The digital data streams from interface unit 20 are then converted or interpreted into readable diagnostic information at the remote location 30 (FIG. 1), and/or by a local network device 60 (FIG. 1) to a local audio/video display. The illustrated design enables diagnostic unit 10 (FIG. 1) to be provided at a reasonable cost.

Interface unit 20 includes a port 264 for receiving and transmitting EKG currents detected by corresponding sensors to an EKG readout apparatus where the EKG currents will be converted or interpreted into readable diagnostic information. Interface unit 20 further includes a fourth, fifth and sixth port 266, 268 and 270, respectively, for receiving and transmitting the conditioned analog outputs from the blood pressure circuitry 222, the temperature circuitry 224 and the oxygen saturation circuitry 226, respectively, to one or more corresponding readout apparatus where the analog outputs will be converted or interpreted into readable diagnostic information.

In one embodiment, interface unit 20 also includes a power supply 272 which supplies power, via power supply distributor 274, to all of the components of the interface unit. Interface unit 20 also preferably includes a plurality of battery packs 276 and a battery charger port 278. An optical isolator 280 electrically isolates the entire interface unit 20 and wearable device 12 (FIG. 1) from any destructive or damaging currents which might be encountered from external communication links.

Figure 3:
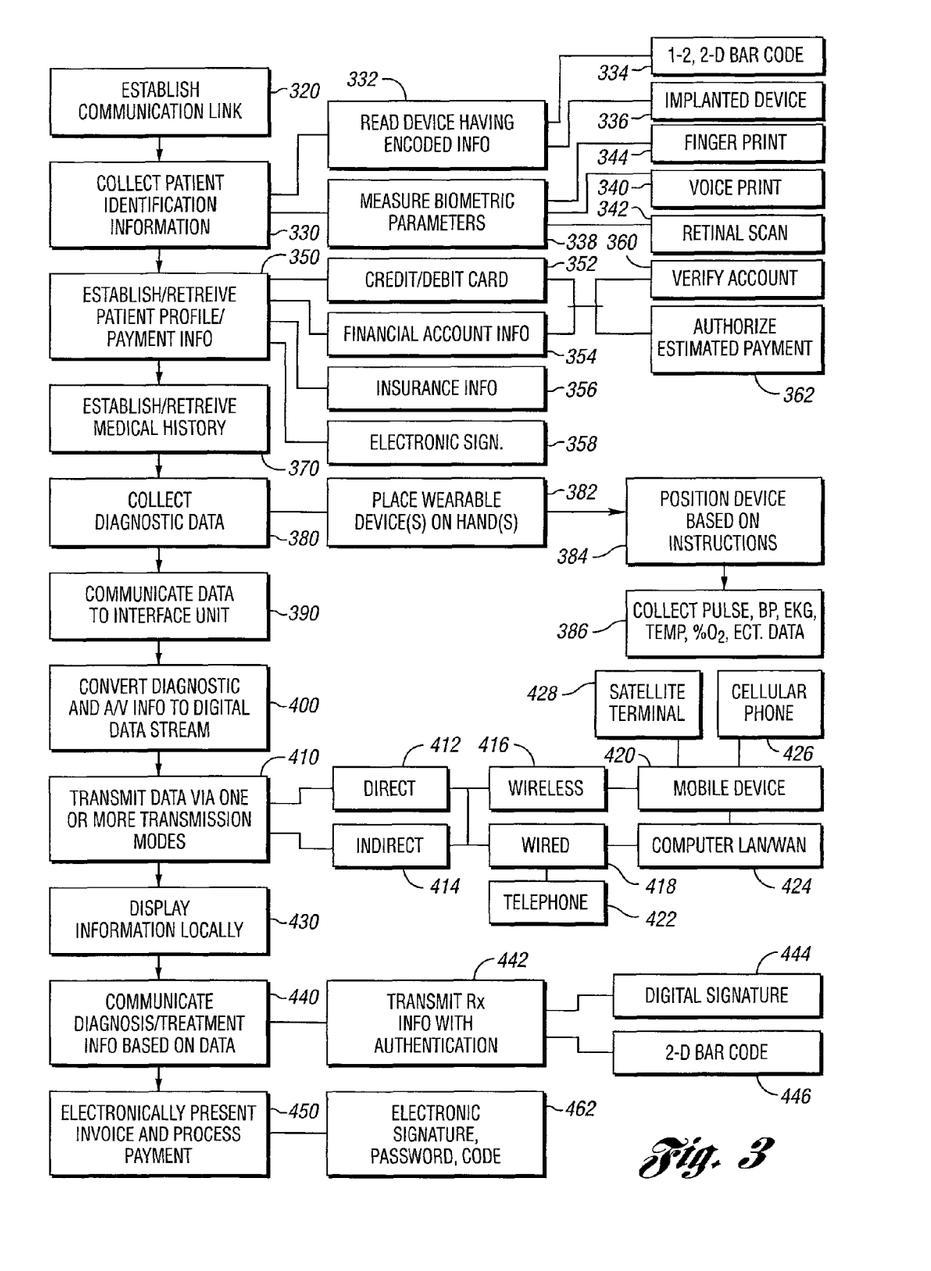
FIG. 3 is a flow chart illustrating a method for medical consultation according to one embodiment of the present invention.

A flowchart illustrating various representative embodiments of a method for medical care and/or consultation according to the present invention is shown in FIG. 3. As will be appreciated by one of ordinary skill in the art, the flowchart illustrated in FIG. 3 includes various steps or functions that are independent of the particular technology used to implement the method. As such, various steps or functions illustrated may be performed in the sequence illustrated, in parallel or in some cases omitted altogether. Likewise, the order of processing or performance illustrated in FIG. 3 is not necessarily required to achieve the objects, features, and advantages of the invention, but is provided for ease of illustration and description.

Preferably, the functions illustrated in FIG. 3 are implemented in a combination of hardware and software executed by a microprocessor-based computer or microcontroller. Of course, various portions or functions of the control logic may be implemented solely by software or solely by hardware. The flowchart of FIG. 3 illustrates one "loop" or pass through the various functions or operations although various operations may be repeated as required by some internal or external event, as known by those of skill in the art.

Block 320 of FIG. 3 represents establishing an audio/video link. As described above, the audio/video link preferably enables real-time two-way communication between a patient and remotely located medical personnel. However, depending upon available communication channel bandwidth and traffic, video and/or audio information may be reduced in quality or frame rate. Identification information is then collected from the patient as represented by block 330. The identification information may be entered by the patient manually using a keyboard, telephone keypad, or other input device, or using voice recognition, for example. Alternatively, patient identification information may be automatically obtained by the patient or another person using a device to read encoded information as represented by block 332. The reader may incorporate various technology to read or retrieve information from a device worn by the patient or implanted in the patient. For example, the reader may incorporate radio frequency (RF), optical, magnetic, inductive, or other technology to retrieve stored or encoded information that may include a patient name, an identification number, and various medical information, such as allergies, medical conditions, and the like. Encoded information may be contained in a one-dimensional or two-dimensional bar-code as represented by block 334, or in an implanted electronic device as represented by block 336. Obtaining identification information may also include the measurement or capturing of patient biometric parameters as represented by block 338. Biometric parameters may include a voice print 340, retinal scan 342, or finger print 344, or any other unique identifying characteristics, for example.

After collecting identification information from the patient, a patient profile may be established or retrieved. The patient profile preferably establishes or retrieves payment information as represented by block 350. Payment information may include a credit/debit card account number and expiration date 352, banking account number and institution routing information 354, and/or insurance information 356. In addition, payment information may require additional authorization such as an electronic signature 358, password, validation code, or the like. For credit/debit card account numbers, the method may include verifying the account number as a valid account number using established algorithms, and/or manually or automatically contacting the card issuer via telephone or computer network as represented by block 360. In addition, this step may include obtaining a payment authorization code for an estimated charge from the card issuer or a test transaction for a financial institution as represented by block 362.

The patient profile also preferably includes medical history information as represented by block 370. Prior to an initial consultation, the patient may be prompted to complete an interactive medical history form for subsequent storage and retrieval from the patient database. Medical history information may include patient biographical information, family history, and diagnostic data obtained from previous consultations. Diagnostic data may include video and/or audio data to facilitate comparison of patient characteristics relative to previous consultations. The video and/or audio information may be collected using the diagnostic device according to the present invention, or alternatively may be provided by transferring digital images of various diagnostic tests to the medical history records of the patient database.

Patient diagnostic data is then collected as represented by block 380. Diagnostic data may be collected by placing the wearable device on a hand (or hands) of the patient or someone other than the patient as represented by block 382. The wearable device is preferably contoured to fit at least a portion of a person's hands and may include one or two gloves, mittens, or pads depending upon the particular application. The wearable device is then positioned over a portion of the patient's body. To assist in proper positioning of the wearable device on the patient's body, instructions may be provided from the remote location using the audio and/or video communication link as represented by block 384. Once properly positioned, the diagnostic device may be used to generate and monitor various signals indicative of corresponding characteristics of the patient including, but not limited to, pulse rate, blood pressure, EKG, percent $O_2$, and temperature as represented by block 386.

The diagnostic data is communicated to an interface unit as represented by block 390. The wearable device may be directly connected to the interface unit or may employ a wireless communication link as illustrated and described above. The interface unit converts the various signals generated by the wearable device and/or the audio/video information to a single digital datastream as represented by block 400. The digital datastream is then transmitted to a remote location using one or more transmission modes as represented by block 410. The particular transmission modes or media may be selected based on available bandwidth and/or quality of service considerations. The diagnostic data is generally assigned a greater importance than the audio/video data but requires lower bandwidth than the audio/video information. As such, depending upon the particular application and implementation, diagnostic data may be transmitted using a first transmission mode with audio/video information transmitted using a second transmission mode. For example, audio/video information may be transmitted using a cable modem over the internet with diagnostic data transmitted via cellular or wired telephone network. The selected transmission mode or modes may provide a direct communication link 412 or an indirect communication link 414. Both direct communication link 412 and indirect communication link 414 may transmit a digital data stream using wireless technology 416 or wired technology 418 via one or more devices, such as mobile device 420, telephone 422, or computer 424. Mobile device 420 may transmit using a cellular telephone network 426, satellite network 428, or the like. In addition to transmitting the diagnostic data to the remote location, information may be displayed locally as represented by block 430.

Diagnosis and/or treatment information based at least in part on the diagnostic data is preferably then communicated by medical personnel from the remote location to the patient as represented by block 440. Treatment information may include audio/video information relative to the diagnosis and proposed treatment delivered to the patient via the two-way communication link. Treatment information may also include control of one or more therapeutic devices incorporated into the wearable diagnostic device. For example, treatment information may control delivery of an electric shock via the defibrillator circuitry and electrodes for a two-glove wearable device worn by someone other than the patient. Alternatively, or in combination, treatment information may include a prescription for medication transmitted to the patient for subsequent presentation to a pharmacist, or transmitted directly to a pharmacy by computer network or telephone as represented by block 442. Prescription information preferably includes encoded authentication information to assure the authenticity of the prescription. The encoded information may include medical personnel authentication information, such as a digital signature as represented by block 444 or a one-dimensional or two-dimensional bar-code as represented by block 446, for example. The authentication information may then be used by the pharmacy in filling the prescription to electronically verify the accuracy and authenticity of the prescription by automatically or manually querying the medical provider database containing authorized prescription information for a particular patient.

Upon completion of the online medical care or consultation, an electronic invoice or receipt may be provided to the patient or a third party for payment as represented by block 450. This step may include obtaining authorization from the patient to process payment for the invoice amount. Patient authorization may include providing an electronic signature, password, or other patient-unique information as represented by block 462.

As should be appreciated by those of ordinary skill in the art, the online medical consultation method according to the present invention may used in a variety of applications or scenarios. Some representative scenarios are described below.

Technician-Provided Out of Office Care—Routine and Emergency

Called by telephone or computer, a responder such as a technician, physician assistant, nurse practitioner or emergency medical technician, depending on level of need, will be immediately dispatched to the patient's home, office or other location. The responder will carry three unique devices for use according to the present invention: a) a high resolution, diagnostic, two-way video camera (which not only can visualize and hear the patient but can detect subtle skin changes, observe eardrums through an otoscope or eyes through an ophthalmoscope and hear heart and lung sounds through a stethoscope, b) a wearable diagnostic device, such as one or two gloves (used for real-time monitoring of ECG, pulse, blood pressure, blood oxygen level, temperature, and more), and c) blood analysis equipment for immediate blood results. The method of the present invention may then employ commercially available and/or unique proprietary communication devices to transmit diagnostic data instantly and in real-time, utilizing the highest bandwidth and/or quality of service transmission mode or pipeline available at the site or supplied by the responder. The responder will also be trained to utilize a variety of treatment options to be used under the direction of the monitoring doctor.

Arriving at the patient's side, the responder will deploy the diagnostic device to establish a communication link and provide two-way audio/video information while transmitting patient identification and diagnostic data to the remote location. A doctor monitors a network device console that displays video from the camera hookup, allows full duplex conversation with the patient and the responder, plays audio from devices, and receives and processes the patient identification and diagnostic data. The doctor will advise the patient, and/or responder, prescribe treatment, or, if needed, order transport of the patient to an office, hospital, or clinic facility. The method of the present invention can be used to respond to various medical situations ranging in urgency and severity from a rash or a cold to a heart attack, brain disorder, trauma or coma, for example. The method provides for on-site treatment and/or stabilization and transport. Everything performed will be under the direct supervision of a physician and digitally recorded for a permanent record in the patient's medical history profile.

When used as described herein, the present invention will likely replace many office calls and emergency room visits. It will provide care to people on ships, at sporting events, or to any location a responder can be sent. The interface unit can communicate via telephone wire, coaxial cable, cellular phone systems, other wireless means and/or by satellite via a satellite terminal (antenna). As such, the reach of the diagnosis and monitoring equipment itself is limited only by available communication technology, which is continually providing increasingly faster communication links to more and more remote locations.

Remote Consultations and Care to Individuals

Individual patients can rent or purchase a diagnostic unit and corresponding services on their own for use in their own home, away from home, or for relatives, for example. The diagnostic unit will automatically connect to a patient's own doctor, if the doctor subscribes to the service, and/or to a participating hospital or medical group of the patient's choice. Doctors would then have the ability to monitor patients with chronic conditions much more effectively using the online consultation method described above. Doctors could also respond more efficiently to many acute but non-emergency questions preventing an unnecessary visit to an urgent care facility or emergency room thereby reducing patient and/or insurance cost and improving patient convenience and outcomes.

On-Site Medical Care

Corporate downsizing and cost cutting have eliminated many in-house medical departments in large corporations. Smaller companies and businesses have never had them. Most schools can afford only a nurse on premise at best. Hotels, arenas, camps, cruise ships, and many other facilities likewise will benefit from availability of affordable medical care. Many do not have a doctor or even a nurse. Those that do still need to rely on external resources for anything other than minor complaints. The accessibility to affordable, high-quality medical care provided by the online consultation method of the present invention will undoubtedly enhance the care available at all these sites and many more.

Home Monitoring

The method of the present invention may also be used to provide cost-effective monitoring services for homebound patients. Video/audio hookups and monitoring devices can be permanently installed in the patient's home and turned off for privacy whenever wanted. The service will respond instantly to distress calls or to problems observed based on the transmitted diagnostic data that patients may not recognize, or for which they might be too ill to call for help. Oxygen and glucose monitors can be implanted under or on the skin that will send warnings when the values range outside of the parameters set by the doctor. Thus, a patient going into heart failure, suffering an asthma attack, or a diabetic crisis will be immediately identified with additional help quickly and efficiently dispatched with a prior knowledge of the patient, medical history, and current crisis.

The present invention also allows relatives or other care givers to talk with and monitor the patient using the real-time audio and video capabilities of the diagnostic device.

Medication Supervision

Many patients respond poorly to treatment because they do not take medications regularly as prescribed. Monitoring devices can be implanted in the dispensing device and when a dose is missed, an immediate reminder may be sent. Programs that employ nurses to visit or call patients to improve compliance have been very successful. Patient care and outcomes are improved and the compliance plans save money over the long term by preventing more expensive problems. The method of the present invention provides a similar alternative at a much lower cost. This type of monitoring and supervision could be applied in many areas.

Information Service

Subscribers using the online consultation method of the present invention could have a "doctor in the house" at all times by having access to medical personnel both through the internet and by direct call. While there may be a wealth of medical information on the internet, very little is interactive or screened for reliability and accuracy. The present invention may cost-effectively employ medical school level expertise in providing useful, accurate, focused information that should be highly attractive to subscribers and attract advertising and site placement fees.

Other Applications

The capabilities of the medical consultation method according to the present invention provides opportunities for numerous other applications including, but not limited to, personalized supervision of home exercise, help in controlling addictions, veterinarian care, and much more.

Thus, the medical consultation method of the present invention provides personal medical care to homes, workplaces, and many other sites effectively delivering medical services to anyone, anywhere, and at anytime.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for remote medical consulting between a patient and medical personnel, the method comprising:
   collecting identification information from the patient;
   wearing at least one wearable device on a hand, the at least one wearable device including at least one diagnostic device for generating signals in response to corresponding characteristics of the patient when positioned over a portion of the patient's body other than hands of the patient;
   positioning the wearable device over a portion of the patient's body other than hands;
   collecting diagnostic data, via the at least one wearable device worn on the hand, from the portion of the patient's body other than the hands of the patient over which the wearable device is positioned;

transmitting the diagnostic data generated using the at least one wearable device to a remote location; and communicating diagnosis and/or treatment information to the patient based at least in part on the diagnostic data.

2. The method of claim 1 further comprising establishing payment information based on the identification information.

3. The method of claim 2 wherein the payment information includes credit or debit card information, the method further comprising:

determining whether the payment information is valid; and automatically obtaining an authorization for payment of an estimated amount for services from a card issuer.

4. The method of claim 2 wherein the payment information includes a banking account number and institution routing number.

5. The method of claim 1 further comprising: accessing a patient database using the identification information to obtain patient medical history information.

6. The method of claim 1 wherein the step of collecting diagnostic information comprises:

positioning the wearable device over a portion of the patient's body in response to video and audio instructions received from the remote location.

7. The method of claim 1 wherein the step of transmitting the diagnostic data comprises wirelessly transmitting the diagnostic data.

8. The method of claim 1 wherein the diagnostic data is transmitted via a first transmission mode and wherein audio data and video images are transmitted via a second transmission mode different from the first transmission mode.

9. The method of claim 1 wherein the step of collecting diagnostic data further comprises collecting EKG data.

10. The method of claim 9 wherein the step of collecting diagnostic data further comprises collecting at least one of pulse rate data, temperature data, and blood pressure data.

11. The method of claim 1 wherein the at least one wearable device comprises a pair of diagnostic devices each adapted for wearing on a respective hand.

12. The method of claim 1 wherein the step of collecting diagnostic data is performed by someone other than the patient.

13. A method for providing medical care comprising:

wearing a wearable device on a hand, the wearable device including a plurality of diagnostic devices for generating signals in response to corresponding characteristics of the patient when positioned over a portion of the patient's body other than hands of the patient;

positioning the wearable device over a portion of the patient's body other than hands;

collecting diagnostic data, via the at least one wearable device worn on the hand, from the portion of the patient's body other than the hands of the patient over which the wearable device is positioned;

converting the diagnostic data to a digital data stream; and transmitting the digital data stream to a location for review by medical personnel.

14. The method of claim 13 further comprising:

combining video and audio data with the digital data stream before transmitting the digital data stream.

15. The method of claim 13 wherein the step of collecting diagnostic data comprises:

placing the wearable device on a hand; and positioning the wearable device over a portion of the patient's body.

16. The method of claim 15 wherein the step of placing the wearable device on a hand comprises placing the wearable device on a patient's hand.

17. The method of claim 15 wherein the step of placing the wearable device on a hand comprises placing the wearable device on a hand of someone other than the patient.

18. The method of claim 13 wherein the wearable device includes two gloves, each having a plurality of diagnostic devices for generating signals in response to a corresponding body characteristic and wherein the step of collecting diagnostic data comprises: placing the gloves on respective hands; and positioning the gloves over portions of the patient's body in response to video and audio instructions received from the medical personnel.

19. The method of claim 13 wherein the step of collecting diagnostic data includes communicating the signals to an interface unit, the method further comprising: wirelessly transmitting the diagnostic data from the interface unit to a display device.

20. The method of claim 19 wherein the display device comprises a cellular telephone.

21. The method of claim 19 wherein the display device comprises a computer.

22. The method of claim 13 further comprising:

communicating diagnosis and/or treatment information based at least in part on the diagnostic data.

23. The method of claim 13 wherein the step of collecting diagnostic data comprises collecting at least pulse rate data, temperature data, and blood pressure data.

24. The method of claim 13 wherein the step of collecting diagnostic data comprises collecting EKG data.

25. A method for remotely providing interaction between a patient and one or more remotely located medical personnel, the method comprising:

obtaining patient identification information;

determining patient payment information based on the identification information;

establishing a two-way video and audio communication link between the patient and the medical personnel;

wearing a wearable device on a hand, the wearable device including a diagnostic device for generating signals in response to corresponding characteristics of the patient when positioned over a portion of the patient's body other than hands of the patient;

positioning the wearable device over a portion of the patient's body other than hands;

collecting diagnostic data, via the at least one wearable device worn on the hand, from the portion of the patient's body other than the hands of the patient over which the wearable device is positioned;

transmitting at least the diagnostic data to the medical personnel; and communicating diagnosis information to the patient based at least in part on the diagnostic data.

26. The method of claim 25 wherein the diagnostic data is transmitted over the internet.

27. The method of claim 25 wherein the step of collecting diagnostic data comprises:

electrically coupling the wearable device to an interface unit; and wirelessly transmitting the diagnostic data from the interface unit to a network access point prior to transmitting the data via a wide area computer network.

28. The method of claim 25 wherein the step of transmitting at least the diagnostic data comprises transmitting the diagnostic data via a cellular telephone.

29. A method for remote medical consulting between a patient and medical personnel, the method comprising:
  collecting identification information from the patient;
  providing a diagnostic device for generating signals in response to corresponding characteristics of the patient when placed over the patient's body other than the patient's hands, wherein the diagnostic device comprises a glove, mitten, or pad with sensors;
  positioning the diagnostic device over a portion of the patient's body other than the patient's hands;
  collecting diagnostic data, via the diagnostic device, from the portion of the patient's body over which the diagnostic device is positioned;
  transmitting the diagnostic data to a remote location; and
  communicating diagnosis and/or treatment information to the patient based at least in part on the diagnostic data.

30. The method of claim 29 wherein collecting diagnostic data comprises placing the diagnostic device on the patient's chest.

31. The method of claim 29 wherein transmitting the diagnostic data comprises transmitting the diagnostic data via a satellite communications network.

32. The method of claim 29 wherein transmitting the diagnostic data comprises wirelessly transmitting the diagnostic data.

33. The method of claim 29 wherein the step of transmitting the diagnostic data to a remote location comprises converting the diagnostic data to a digital data stream and transmitting the digital data stream to a location for review by medical personnel.

34. The method of claim 29 wherein the step of collecting diagnostic data is performed by someone other than the patient.

35. A method for providing medical care comprising:
  wearing a wearable device on a hand, the wearable device including a diagnostic device for generating signals in response to corresponding characteristics of a patient when positioned over a portion of the patient's body other than hands of the patient;
  positioning the wearable device over a portion of the patient's body other than hands;
  collecting diagnostic data, via the at least one wearable device worn on the hand, from the portion of the patient's body other than the hands of the patient over which the wearable device is positioned; and
  transmitting the diagnostic data to a remote location for review by medical personnel.

* * * * *